US010052177B2

(12) United States Patent
Andreiko (10) Patent No.: US 10,052,177 B2
(45) Date of Patent: Aug. 21, 2018

(54) CUSTOM ORTHODONTIC BRACKET PLACEMENT JIG AND JIG MAKING METHOD AND APPARATUS

(75) Inventor: Craig A. Andreiko, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 1228 days.

(21) Appl. No.: 11/464,909

(22) Filed: Aug. 16, 2006

(65) Prior Publication Data

US 2007/0031775 A1 Feb. 8, 2007

Related U.S. Application Data

(63) Continuation-in-part of application No. 10/156,162, filed on May 28, 2002, now Pat. No. 7,094,053.

(51) Int. Cl.
*A61C 3/00* (2006.01)
*A61C 7/14* (2006.01)

(52) U.S. Cl.
CPC .................... *A61C 7/146* (2013.01)

(58) Field of Classification Search
CPC ..................................... A61C 7/146
USPC ........... 433/18, 22, 24, 6, 2–3, 8–12
See application file for complete search history.

(56) References Cited

U.S. PATENT DOCUMENTS

| | | | |
|---|---|---|---|
| 2,302,376 A * | 11/1942 | Myerson | 433/26 |
| 3,521,355 A | 7/1970 | Pearlman | |
| 4,657,508 A * | 4/1987 | Dellinger | 433/24 |
| 5,114,339 A | 5/1992 | Guis | |
| 5,121,334 A | 6/1992 | Riley et al. | |
| 5,368,478 A | 11/1994 | Andreiko et al. | |
| 5,542,842 A | 8/1996 | Andreiko et al. | |
| 5,683,243 A * | 11/1997 | Andreiko et al. | 433/3 |
| 5,863,198 A * | 1/1999 | Doyle | 433/3 |
| 5,879,158 A | 3/1999 | Doyle et al. | |
| 2002/0025503 A1 | 2/2002 | Chapoulaud et al. | |

(Continued)

FOREIGN PATENT DOCUMENTS

| | | |
|---|---|---|
| FR | 2840192 A | 12/2003 |
| FR | 2871080 A | 12/2005 |
| JP | 58137005 A | 8/1983 |

OTHER PUBLICATIONS

French Patent Office, Preliminary Search Report from French counterpart application No. 0705059, dated Apr. 23, 2008.

*Primary Examiner* — Yogesh Patel
(74) *Attorney, Agent, or Firm* — Wood Herron & Evans LLP (57) ABSTRACT

A placement jig for locating an orthodontic appliance on a tooth is provided with a cavity formed in a jig body and conforming to the contour of an occlusal portion a tooth crown, which cavity is coated with a releasable adhesive to hold the jig to the tooth as the appliance is bonded to the tooth. Connecting structure is fixed to the jig body. In certain embodiments, at least two jig-locating areas shaped to respectively conform to areas on the occlusal surfaces of two different teeth of a group are machined into the machinable material, and appliance receiving structures are also machined on each jig body, each for holding an orthodontic appliance in a fixed position and orientation relative to the jig body. The jig bodies for placing orthodontic appliances on the teeth of an individual patient are preferably formed of a single piece of machinable material. A method and an apparatus for forming the jig bodies are provided.

11 Claims, 5 Drawing Sheets

(56) References Cited

U.S. PATENT DOCUMENTS

2002/0028417 A1\* 3/2002 Chapoulaud et al. .......... 433/24
2003/0224310 A1 12/2003 Andreiko
2005/0003321 A1\* 1/2005 Wiechmann et al. ............ 433/9
2006/0084026 A1 4/2006 Cinader et al.
2006/0084030 A1 4/2006 Phan et al.

\* cited by examiner

CUSTOM ORTHODONTIC BRACKET PLACEMENT JIG AND JIG MAKING METHOD AND APPARATUS

This is a Continuation-In-Part of U.S. patent application Ser. No. 10/156,162, filed May 28, 2002, U.S. Publication No. 2003/0224310, hereby expressly incorporated herein by reference.

This application is also related to U.S. patent application Ser. No. 09/941,151, filed Aug. 28, 2001, and International Patent Application No. PCT/US00/35558, filed Dec. 29, 2000, now U.S. Publication No. US-2002/0028417, and U.S. Provisional Patent Application Ser. No. 60/173,890, filed Dec. 29, 1999, all of which are hereby expressly incorporated herein by reference in their entirety.

FIELD OF THE INVENTION

This invention relates to the positioning of orthodontic appliances on teeth and, more particularly, to appliance positioning jigs and to the manufacture and use of such jigs, especially custom jigs for the positioning of orthodontic appliances.

BACKGROUND OF THE INVENTION

Orthodontic appliances to position the teeth of patients are designed to contact the teeth of a patient and apply forces to those teeth that will cause the teeth to move toward an arrangement that the orthodontist determines to be ideal or to otherwise satisfy a treatment objective. Goals of orthodontic treatment include moving the teeth of a patient as closely as possible to the finish tooth positions determined ideal for achieving the desired treatment result, minimizing the time during which the patient must wear the appliances used for the treatment, and minimizing the time of the orthodontic practitioners, or chair-time, in treating the patients. All of these goals are served by reducing the amount of manual adjustment of the appliances, such as wire bending, needed by the orthodontic practitioner, during the course of the treatment of a patient with an appliance.

A most common and useful type of orthodontic appliance includes a set of brackets bonded to each of the respective teeth of a patient that support and are interconnected by a resilient archwire. The archwire is elastically deformed from its unstressed shape and applies forces to the teeth through the brackets as the wire tends to return to its unstressed shape. The trend in appliance design or selection is to employ an archwire having a predetermined shape that, when mounted on brackets secured to the teeth at predetermined design positions, will urge those teeth toward desired treatment positions without, or with minimal, intervention by the orthodontist in bending the wire. Standard appliances that are designed to anatomical averages typically require some adjustment during the course of a patient's treatment. Custom appliances ideally eliminate or minimize this need for adjustment. For the goals of minimal or no archwire adjustment to be met, however, brackets must be accurately placed on the patient's teeth at exact positions for which the appliance was designed.

For accurate placement of orthodontic brackets onto the teeth of a patient, the use of custom placement jigs has been proposed. Such jigs have been described, for example, in U.S. Pat. No. 5,368,478 and International Patent Application No. PCT/US00/35558, hereby incorporated herein by reference, to place brackets of orthodontic appliances. Such jigs may include a precision formed custom surface that is manufactured from tooth crown-shape data that has been scanned from the patient's teeth. Each such surface is intended to precisely fit over the crown of a patient's respective tooth and to hold a bracket of an orthodontic appliance against its proper design position on the tooth while the bracket is being bonded to the tooth surface.

Placing brackets individually can be time consuming, and jigs that contact a single tooth crown can require careful handling to ensure precise bracket placement. On the other hand, whole-arch trays for placing multiple brackets simultaneously can encounter interferences with teeth and have proved difficult to handle and use.

While the provision of such jigs has gone far to serve the orthodontic objectives discussed above, there remains a need to improve the function and handling of such jigs to better serve these orthodontic objectives.

SUMMARY OF THE INVENTION

A primary objective of the present invention is to optimize the efficiency and accuracy in orthodontic appliance placement.

Objectives of the invention include providing jigs for positioning orthodontic appliances on teeth, and particularly, jigs that can easily, efficiently and reliably be used by orthodontic practitioners to place appliances for bonding to the teeth of a patient. A particular objective of the invention is to provide an orthodontic appliance and jig combination that can be easily and accurately placed on the tooth of a patient by an orthodontic practitioner.

Further objectives of the invention include providing orthodontic appliance placement jigs and orthodontic appliance and jig combinations that can be easily and accurately placed on one or more teeth of a patient by an orthodontic practitioner and easily maintained on the teeth while the appliance is being bonded.

Another objective of the invention is to provide an efficient method and apparatus for making orthodontic appliance positioning jigs.

According to principles of the present invention, an orthodontic appliance positioning jig is provided having jig locating surfaces that conform to at least a portion of the crown of one or more teeth of the individual patient being treated or that contact one or more appliances so as to locate the appliances on the teeth for bonding.

The jig may be provided with an appliance connecting feature to removably hold the jig to the appliance for which the jig is designed to bond the appliance to the tooth. The jig may also be provided with a crown connecting feature to removably hold the jig and appliance combination to a tooth.

According to a preferred and illustrated embodiment of the invention, an orthodontic appliance placement jig is configured so that the jig, when combined with one or more appliances, provides a plurality of contact areas on the crowns of a plurality of teeth of the patient. The contact areas are shaped and spaced to optimize positioning and orienting of the appliances on the teeth for bonding. For example, a jig body may have two or more crown conforming contact areas configured to engage the occlusal surfaces of two or more specific teeth, and may support one or more brackets with their bases positioned to contact the facial surfaces of specific teeth. An embodiment for mounting brackets on two to six adjacent teeth with the jig body contoured to contact areas on the occlusal surfaces of the end two of the adjacent teeth provides efficient and accurate bracket placement. Jigs for three or four adjacent teeth are particularly useful and efficient.

According to other principles of the invention, contact areas on a jig-locating surface are coated with a releasable adhesive, such as a pressure sensitive or other tacky adhesive for example, that temporarily holds the jig to the tooth while the jig holds an orthodontic appliance that is connected to the jig in a position on the tooth for bonding. The releasable adhesive keeps the appliance in place while the appliance is being bonded to the tooth with an orthodontic or other dental adhesive, without relying on the practitioner to manually hold the jig during the time that the dental adhesive is setting or being cured.

In one described embodiment of the invention, a custom placement jig is provided with a rigid foam body having one or more custom crown-conforming cavities that have been formed therein by a computerized three-dimensional manufacturing process to conform to the precise shape of occlusal portions of the crowns of a patient's tooth. The surfaces of the cavities are coated with a contact adhesive, a pressure sensitive adhesive or other releasable adhesive, to hold the jig to the tooth as the appliance is being bonded to the tooth.

The invention provides for the efficient and accurate placement of orthodontic appliances on the teeth of patients.

The features described herein are particularly useful for custom placement jigs that are useful in placing standard or custom orthodontic appliances. Furthermore, certain of the features described herein are also useful for placement jigs that are not customized for individual patients.

Other objectives and advantages of the invention are more specifically set forth in the parent application U.S. Patent Publication No. 2003/0224310.

These and other objectives and advantages of the present invention will be more readily apparent from the following detailed description of the drawings, in which:

DETAILED DESCRIPTION OF THE DRAWINGS

Figure 1:
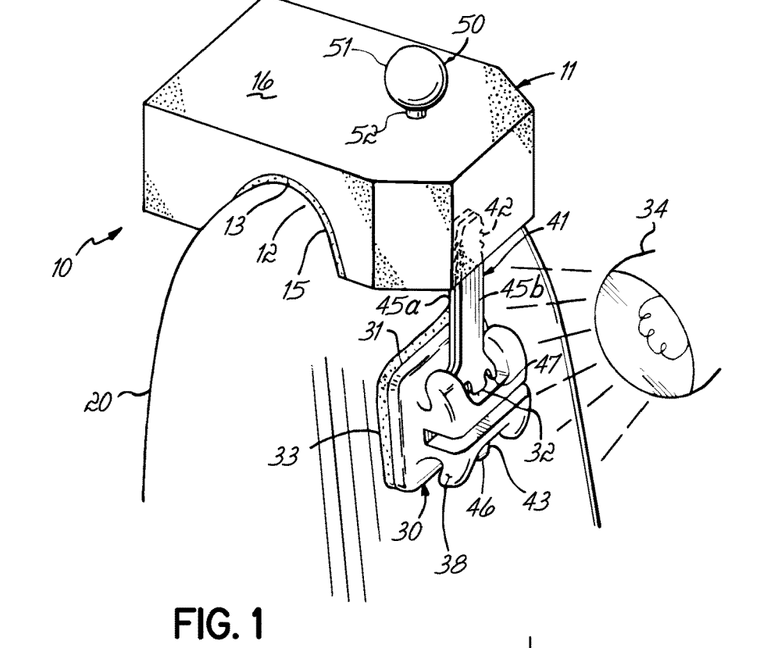
FIG. 1 is a perspective view of an orthodontic bracket placement jig, according to certain embodiments of the present invention, illustrated in combination with an orthodontic bracket, being placed in position on the crown of a tooth of a patient.

FIG. 1 illustrates an embodiment of a positioning jig 10 for use in locating an orthodontic appliance on a patient's tooth for bonding. The jig 10 includes a jig body 11 formed of a single piece of material. A cavity, socket or concave depression 12 is machined into the jig body 11. The wall of the cavity 12 in the body 11 functions as a jig locating surface 13 that is configured to conform precisely to a unique portion of the crown of one of the teeth of a patient, preferably to a portion of the crown approximately centered on the occlusal surface of the tooth.

In FIG. 1 the jig 10 is illustrated with the jig-locating surface 13 positioned on an area of the crown of the tooth 20 that is generally centered on the occlusal edge of a tooth 20 of a patient, which tooth 20 is illustrated as a lower central incisor of the patient. The jig 10 is shown holding an orthodontic appliance in the form of an orthodontic bracket 30, which has a bonding base or pad 31 to which extends an archwire support 38 having an archwire slot therein. The jig 10 is shown holding the bracket 30 with its bonding base 31 against the facial side of the tooth 20 in the position in which it was designed to function as part of an orthodontic appliance set that was preferably custom designed for the treatment of the specific patient. Orthodontic brackets are currently the type of appliance most often placed using jigs described herein, but the jig 10 may be used to position other types of appliances or appliance securing or aligning structures on teeth. Such a bracket 30, when its base is bonded to the tooth 20 in this position, is typically interconnected by an orthodontic archwire (not shown) of the orthodontic appliance set, of which the bracket 30 is a component, to brackets similarly designed for and bonded to other teeth of the patient.

The material of which the body 11 of the jig 10 is made may be any economical rigid material that is compatible with oral orthodontic treatment and can be formed with sufficient precision and at sufficiently low cost into a placement jig capable of settling in a unique predetermined position on the crown of a patient's tooth when placed on the crown and urged against it with a minimal force applied by the hand of an orthodontic practitioner. A foam material, such as a rigid foam material or a compliant foam material, is useful. A rigid foam material, for example, such as the prototyping material sold by General Plastics Mfg. Co. of Tacoma, Wash., under the name LAST-A-FOAM, has been found suitable. This foam material can be milled with a precision computer-controlled cutting tool driven by three-dimensional data that defines the shape of the crown of the patient's tooth. Such data may be that derived, for example, by scanning systems referred to in the related applications identified above and incorporated by reference. Alternatively, the body 11 of the jig 10 may be molded, for example of thermoplastic or thermosetting material or of some other moldable material. When molded, the mold may, in turn, be formed by computer-controlled equipment to conform to the three-dimensional portion of a crown of the patient's tooth.

According to one feature of the invention, a releasable adhesive coating 15 covers the surface 13 that lines the cavity 12. The adhesive coating 15 holds the jig 10 on the crown of the tooth 20 in the position in which it was placed by the practitioner, and holds the base 31 of the bracket 30 against the surface of the tooth in the position at which it is to be bonded so that the practitioner need not continue to hold the combination as the dental adhesive 33 being used to bond the base 31 to the tooth surface cures. The releasable adhesive may be any of several types of adhesive, such as a pressure sensitive adhesive. One acceptable adhesive that can be used for the coating 15 is an acrylic emulsion adhesive marketed under the trademarks PROS-AIDE and PROS-AIDE II by Cybergraphic Designs, Inc.

According to another feature of the invention, orthodontic appliance connecting structure may be provided on the jig body 11. The appliance connecting structure is configured so that it holds the appliance to the jig for transporting to the patient's tooth, but can release the appliance once the appliance is bonded to the tooth, leaving the appliance on the tooth as the jig is removed from the tooth crown. In the illustrated embodiment, the appliance connecting structure is in the form of a pin or peg 41 that is fixed to the jig body 11. The peg 21 slips into and out of a hole 32 in the bracket 30 when the jig is respectively moved occlusally and gingivally onto and off of the crown of the tooth and relative to a bracket 30 that is mounted in its design position on the crown of the tooth, typically in a vertical direction. In the orientation illustrated in FIG. 1 with the tooth 20 being a lower tooth, the pin 41 is fixed to the jig body 11 at its proximate end 42 and has a remote end 43 that is dimensioned to form a friction fit with the sides of the hole 32 in the bracket 30. In the embodiment shown, the remote lower end 43 of the peg 41 is formed of two spring metal members 44a,44b that are spring biased to expand away from each other. The hole 32 in the bracket 30 is a specially configured cooperating structure on the appliance that is designed to function with the peg end 43 to releasably carry the bracket 30 on the jig 10.

According to another feature of the invention, handle structure 50 may be provided on the body 11 of the jig 10. The handle structure 50, if provided, is preferably located on a surface 16 of the jig body 11 that is opposite the surface 12. The handle structure 50 is configured to be gripped by tweezers or some other hand tool by the orthodontic practitioner. In FIG. 1, the handle structure 50 is illustrated as a generally spherical knob or ball 51. The knob or ball 51 has a post 52 that is fixed to and extends the ball 51 away from the surface 16 of the jig body 11. This handle structure 50 is positioned generally directly over the occlusal edge of the tooth 20 or slightly to the facial side thereof, so that downward or upward force can be applied to the handle without the jig and appliance rotating about a horizontal axis as the jig is placed on or removed from the tooth. Preferably, but not necessarily, special tweezers may be used to grip the ball 51 of the handle structure 50.

Referring still to FIG. 1, a jig 10 having a handle 50 is attached to an orthodontic bracket 30, which is connected to the jig body 11 by the peg 41. The bracket 30 is generally oriented on the peg 41 so that the pad or base 31 of the bracket 30 faces toward the cavity 12 of the bracket body 11. The bracket 30 is somewhat rotatable on the peg 41 so that small mis-orientation will automatically be corrected when the jig-locating surface 13 is positioned on the crown of the proper tooth. The base 31 of the bracket 30, before being placed against the tooth 20, is coated with a dental adhesive 33 of any of a number of types used to bond orthodontic appliances to teeth. Such adhesive may be of a type applied by the practitioner before placing the appliance on the tooth or may be of a type that is applied to the bracket upon manufacture or by the orthodontic appliance supply company before being provided to the orthodontic practitioner.

This combination of jig 10 and bracket 30 is picked-up by an orthodontic practitioner and orients the combination over the crown of the tooth 20 of the patient. Then the practitioner lowers the combination onto the tooth 20 by lightly pressing the jig-locating surface 13 against the occlusal edge of the tooth 20 and seating the cavity, which is comparable to a negative impression of a portion of the occlusal surface of the tooth 20, at a unique position and orientation on the crown of the tooth 20 with the base 31 of the bracket 30 in its correct bonding position against the facial side of the tooth 20, as illustrated in FIG. 1.

Once the jig 10 is on the tooth 20, the tacky adhesive 15 holds the jig 10 to the tooth 20. The practitioner may then release the jig while the adhesive on the base 31 of the bracket 30 is set. Where UV curable adhesive is used, the curing is brought about by exposure of the adhesive to ultraviolet light from a curing gun 34 applied by the practitioner. At this stage, the tacky adhesive 15 holds the jig 10 and the bracket 30 in place, freeing the hands of the practitioner.

After the dental adhesive 33 has set and the bracket 30 is bonded to the tooth 20, the practitioner can engage the jig 10 and move it occlusally away from the tooth 20, causing the tacky adhesive 15 to release from the crown of the tooth 20 and the remote end 43 of the peg 41 to slide out of the hole 32 in the bracket 30, leaving the bracket 30 bonded to the tooth 20. Then, the practitioner can remove the jig 10 from the patient's mouth.

The peg 41 of the jig 10 may be formed, for example, as illustrated and described in the parent application No. 2003/0224310, of a strip of spring sheet metal that has been die cut to define two matching halves 45a,45b and folded so that the halves 45a,45b form two layers joined at the juncture of the halves 45a,45b, which defines a tip 46 of the peg 41 at the remote end 43 of the peg 41. Outwardly extending stop wings 47, die-cut or otherwise formed in the sides of the strip halves 45a,45b, positively limit the distance that the remote end 43 of the peg 41 moves into the hole 32 of the bracket 30, to thereby precisely control the position of the bracket 30 relative to the body 11 of the jig 10.

Once the peg 41 is fixed to the body 11 of the jig 10 with the end 42 of the peg 41 inserted into the hole in the body 11, the peg 41 is not easily removable from the body 11. On the other hand, placement of the remote end 43 of the peg 41 into the hole 32 of the bracket 30 holds the bracket 30 to the jig 10 with enough friction to prevent the bracket 30 from falling off of the peg 41 when the assembly is being moved, but with a low enough friction to allow the jig 10 to be easily removed from the bracket 30 once the bracket 30 is bonded to the tooth 20.

The peg 41 is fixed to the body 11 of the jig 10 in a precise position relative to the cavity 12 in the jig body 11. The cavity 12 uniquely locates the jig 10 on the occlusal surface on the crown of the tooth 20. The base 31 of the bracket 30 is located at a precise design position and orientation relative to the hole 32 in the archwire support 38 of the bracket 20 so that the bracket 20 will be positioned by the jig 10 at its predetermined position on the tooth 20. As a result, placement of the jig 10 on the tooth 20, with the cavity 12 uniquely positioned on the crown of the tooth 20, locates the base 31 of the bracket 30 in its exact design position on the surface of the crown of the tooth 20 for bonding to the tooth.

Figure 2:
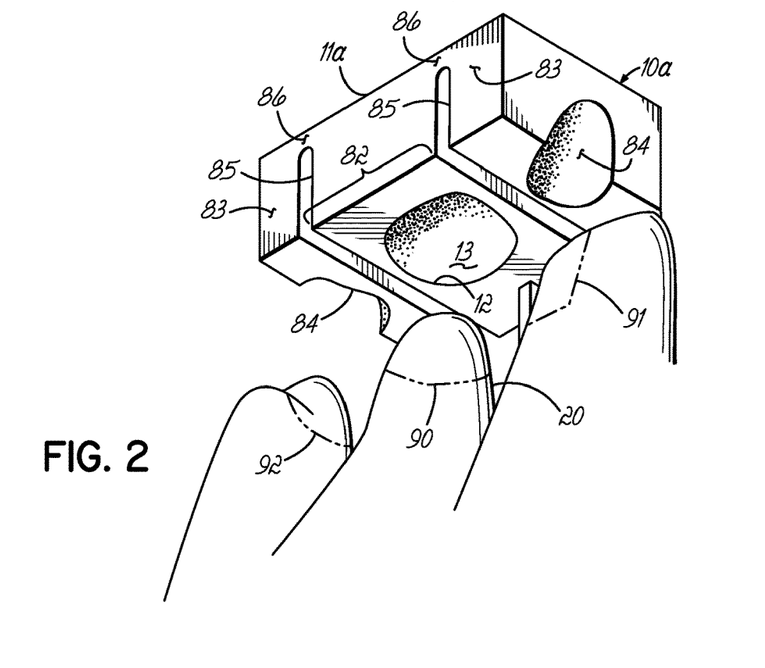
FIG. 2 is a perspective view of another embodiment of the jig according to principles of the present invention.

In FIG. 2, a jig 10b is illustrated having a feature that facilitates the registration of the jig on a tooth. The jig 10a is provided with a wide body 11a having a central section 82 that has a cavity 12 formed therein, in the same manner as with the jig 10 described above, having a surface 13 that conforms to the three-dimensional shape of the crown of the tooth. Additionally, the body 11a is provided with one or two side extensions 83 configured to contact a portion 91,92 of the crown of one or both adjacent teeth. Each of the side sections 83 has a cavity or depression 84 therein having a surface that is formed to the three-dimensional shape of a portion of the crown of one of the adjacent teeth. This portion 91,92 of the crown of an adjacent tooth may be a small portion on or near the mesial or distal edge of the adjacent tooth.

The locations of the depressions 84 are located on the body 11a relative to the central cavity 12 based on three-dimensional scan data of the teeth in their pre-treatment malocclused condition. The jig 10a with the side sections 83 ceases to be able to accurately use adjacent teeth for registration as the teeth move from their initial positions, rendering them less useful for subsequent placement of an appliance that has to be rebonded later in the treatment. Such rebonding may be necessary where a bond fails or when an appliance must be removed and replaced for some other reason. To make jigs 11a reusable, the side sections 83 are separated from the central section 82 of the body 11b by a slot 85 and are connected to the central section 82 by a narrow web 86, which can be broken to remove the side sections 83 from the central section 82, thereby rendering the jig 11a reusable for rebonding of an appliance later in the course of treatment.

Figure 3:
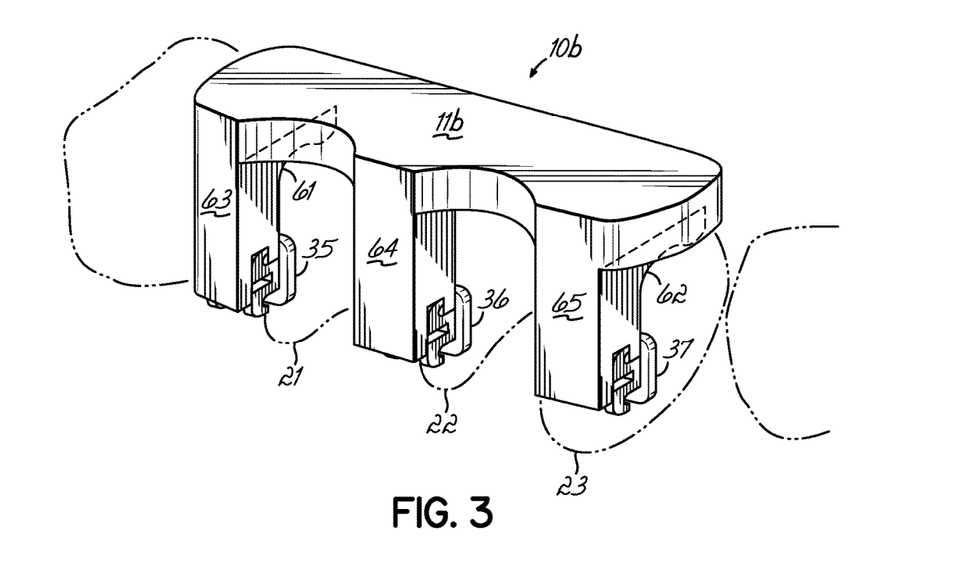
FIG. 3 is a perspective view of a jig according to the invention, shown in an embodiment for placing orthodontic brackets on three adjacent teeth.

FIG. 3 shows a jig 10b that facilitates registration on a plurality of the teeth of a patient, shown here as three adjacent teeth including a lower right second bicuspid 21, a lower right first bicuspid 22 and a lower right cuspid, 23. The jig 10b also has a wide body 11b that extends across the crowns of the three teeth. The body 11b has two crown-conforming surface areas 61 and 62 that are configured to conform to different portions of the occlusal surfaces of the crowns of two teeth, for example, of the end most teeth of the group of adjacent teeth, namely the second bicuspid 21 and the cuspid 23. The body 11b also includes three bracket supports or receivers 63, 64 and 65, each configured to receive and hold an orthodontic bracket 35, 36 and 37, respectively, that is specifically designed for mounting on a respective one of the teeth. Here, the bracket 35 is configured for the lower right second bicuspid 21, the bracket 36 is configured for the lower right first bicuspid 22 and the bracket 37 is configured for the lower right cuspid 23. The body 11b is further configured so that, when the brackets 35-37 are held by the receivers 63-65 respectfully, their bases contact and conform to portions of the facial sides of the respective teeth 21-23, when the jig 10b is registered on the teeth with the areas 61 and 62 conforming to occlusal portions of the crowns of the teeth 21 and 23, and when the teeth are in their pre-treatment, maloccluded positions.

The jigs 10b are most useful in placing on teeth, brackets of custom orthodontic appliances, or appliances in other situations where three-dimensional scans of the surfaces of the patient's teeth are available. As described, for example, in International Patent Application No. PCT/US00/35558 [U.S. Publication No. US-2002/0028417-A1], referred to above, bracket placement jigs can be made by scanning the teeth of the patient to produce a digital model of the patient's teeth. Tooth shaped data from the model is used to produce the contoured cavities 61 and 62 that conform to the crowns of the patient's teeth. Further, the scan is made with the teeth in their initial positions prior to orthodontic treatment, so that the different cavities 61 and 62 can be made to conform to areas on two different teeth that bear the same spacial relationship to the scan data used to define the cavities 61 and 62. In addition, the areas should be picked for the quality of the tooth-shaped data available. For example, where high resolution actual data is available for certain areas of the teeth, those areas should be used over areas defined only by low resolution data. These areas, in turn should be used over areas defined by interpolated or estimated data. In this way, the jig body 11b will precisely register against areas of two of the teeth of a group of teeth.

Furthermore, with custom orthodontic appliances, it is possible to conform the bases of the brackets 35-37 to conform on an individual basis to the facial sides of the crowns of the patient's teeth to which they are to be bonded. Even where the appliance is not custom or is not completely customized, bracket bases can be curved to conform to the average contours of the respective teeth. As a result, when the brackets 35-37 are supported in the receivers 63-65, the pads of the brackets 35-37 conform at least generally to the facial surfaces of the crowns of the teeth 21-23, respectively. This provides to the overall combination of the jig 10b and the brackets 35-37 the ability to be registered against the three teeth 21-23, providing five points of contact between the jig and bracket assembly and the teeth. Two contact points are provided on the occlusal side of the teeth by the cavities 61 and 62, while three contact points are provided on the facial sides of the teeth. This provides highly precise placement of the brackets on the maloccluded teeth.

Figure 4:
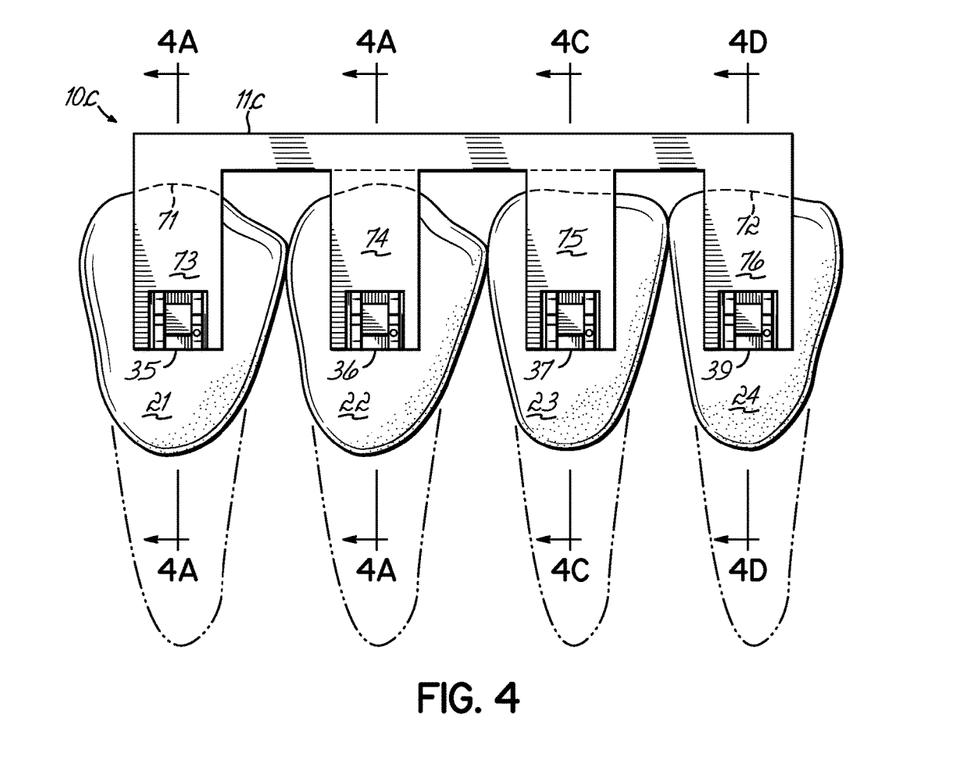
FIG. 4 is a facial view of a jig and bracket combination, shown in an embodiment for placing brackets on four adjacent teeth.
Figure 4A:
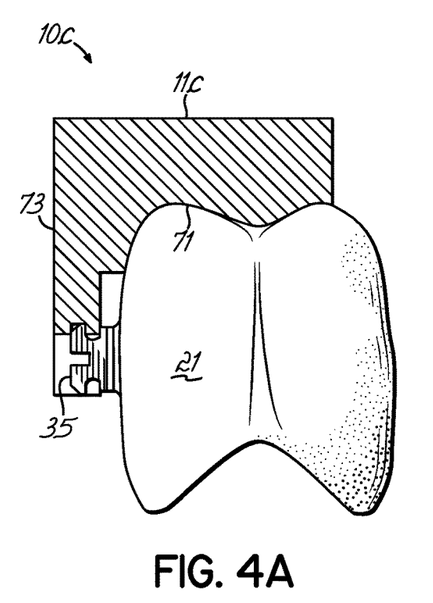
FIGS. 4A-D are schematic cross-sectional views along lines 4A-4A through 4D-4D, respectively, of FIG. 4.
Figure 4B:
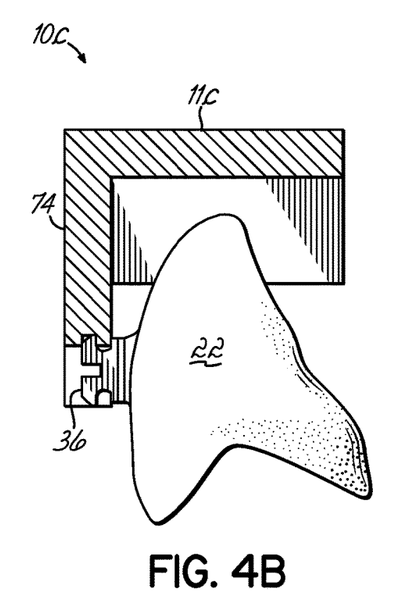
Figure 4C:
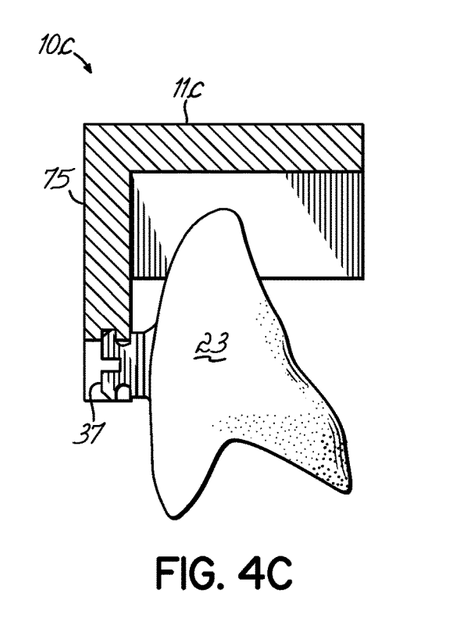
Figure 4D:
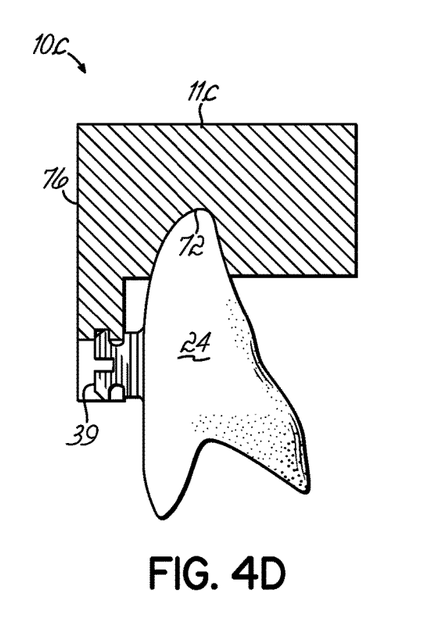

Multi-tooth jigs such as jig 10b can be made for groups of from two to six adjacent teeth. Jig 10c, illustrated in FIG. 4, applies brackets 35-37 and 39 to four adjacent teeth, for example, teeth 21-23 plus the lower right lateral 24. The jig 10c has a wide body 11c that extends across the crowns of the four teeth 21-24. The body 11c also has two crown-conforming surface areas, including area 71 that is configured to conform to a portion of the occlusal surface of the crown of the second bicuspid 21, and area 72 that is configured to conform to a portion of the occlusal surface of the crown of the lateral 24. The areas 71 and 72 are on two different teeth of the group, which are preferably, but need not necessarily be, the two end most teeth of the group. The body 11c also includes four bracket supports or receivers 73, 74, 75 and 76, each configured to receive and hold an orthodontic bracket 35, 36, 37 and 39, respectively.

The cross-sectional views of FIGS. 4A-4D illustrate the cavities 71 and 72 in detail against the occlusal surfaces of the teeth 21 and 24, and shows that the jig body 11c does not contact the occlusal surfaces of the teeth 22 and 23. The minimal surface contact at two areas on occlusal surfaces of the teeth of the group, plus the contact of the bracket bases against the facial areas of the teeth, provide positive, exact registration with the teeth while minimizing error and interference. This allows the orthodontist to place plural brackets simultaneously on groups of adjacent teeth.

Figure 5A:
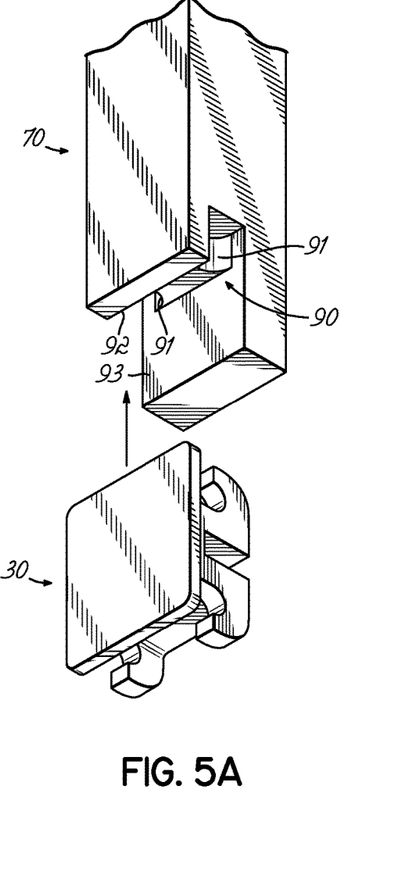
FIGS. 5A and 5B are perspective views showing a receiver portion of the jig of FIG. 4.
Figure 5B:
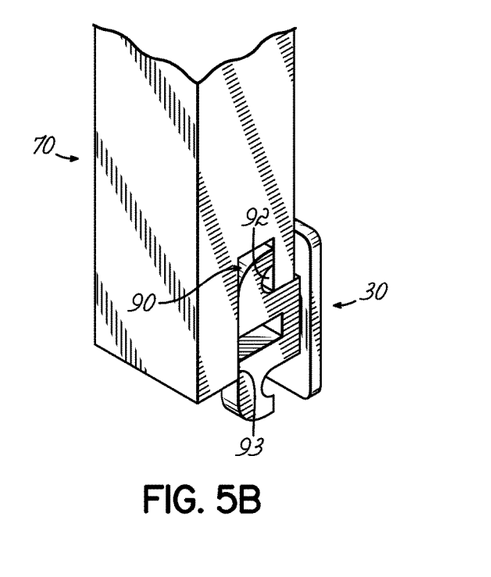

The receiver portions of the jig bodies 11b and 11c, referred to above as receivers 63-65 and 73-76, are illustrated in detail as receiver 70 in FIGS. 5A-5B. The receivers 70 extend from and are integrally formed of the jig bodies 11. Each receiver 70 has formed therein a recess 90 for receiving and holding a specific one of the brackets 30 of an orthodontic brace in a specific position and orientation relative to the rest of the jig body 11. The recess 90 includes cutouts 91 configured to receive the tie wings of a bracket 30 and has opposed clamping surfaces 92 and 93 configured to hold in place and retain a bracket 30 placed in the recess 90. The brackets 30 are usually loaded into the jigs 10 at the appliance manufacturing facility from which the orthodontic appliance is ordered, particularly where the appliance is a fully customized orthodontic appliance. Preferably, the brackets 30 are secured in the recesses 90 with the use of an adhesive, for example, a food grade adhesive such as a PVA (poly vinyl alcohol) adhesive. One suitable adhesive is that manufactured by the Borden company under the name ELMER'S WASHABLE SCHOOL GLUE. Such a glue forms a rigid bond, but one that can be broken to remove the jig from the teeth after the brackets have been bonded to the teeth.

Jigs having the features described above can be used to place one or more orthodontic appliances, for example brackets, on one to six teeth on a group of from two to six adjacent teeth of a patient. The jig body will have at least two tooth-crown-conforming areas that make contact with corresponding areas on the occlusal surfaces of at least two different teeth of the group. In addition, the jig, when assembled with the at least one appliance, the at least one appliance will also make contact with the facial surface of at least one tooth of the group. The at least one appliance is one that has been designed or selected for placement on a specific tooth of the group. The assembled combination of jig body and the one or more appliances will thereby make contact with at least three areas on the surfaces of the crowns of teeth of the group to position the appliances for bonding to the teeth. The relative positions of the areas on the assembled combination correspond to predetermined contact areas on the teeth of the group when the teeth are in the initial positions and orientations that they occupy in the mouth of the patient prior to the commencement of the orthodontic treatment by which the teeth are to be moved by the appliances being placed.

Manufacture of jigs 10 can be accomplished by any of several methods using various types of equipment responsive to three-dimensional data of the patients teeth in their initial pre-treatment positions. Machining is an economical and precise technique, through stereo-lithography, molding (e.g., in molds made on 3D data driven equipment) and other techniques can be used. A device 100 for machining the jigs 10, described above, is illustrated in FIG. 6.

Figure 6:
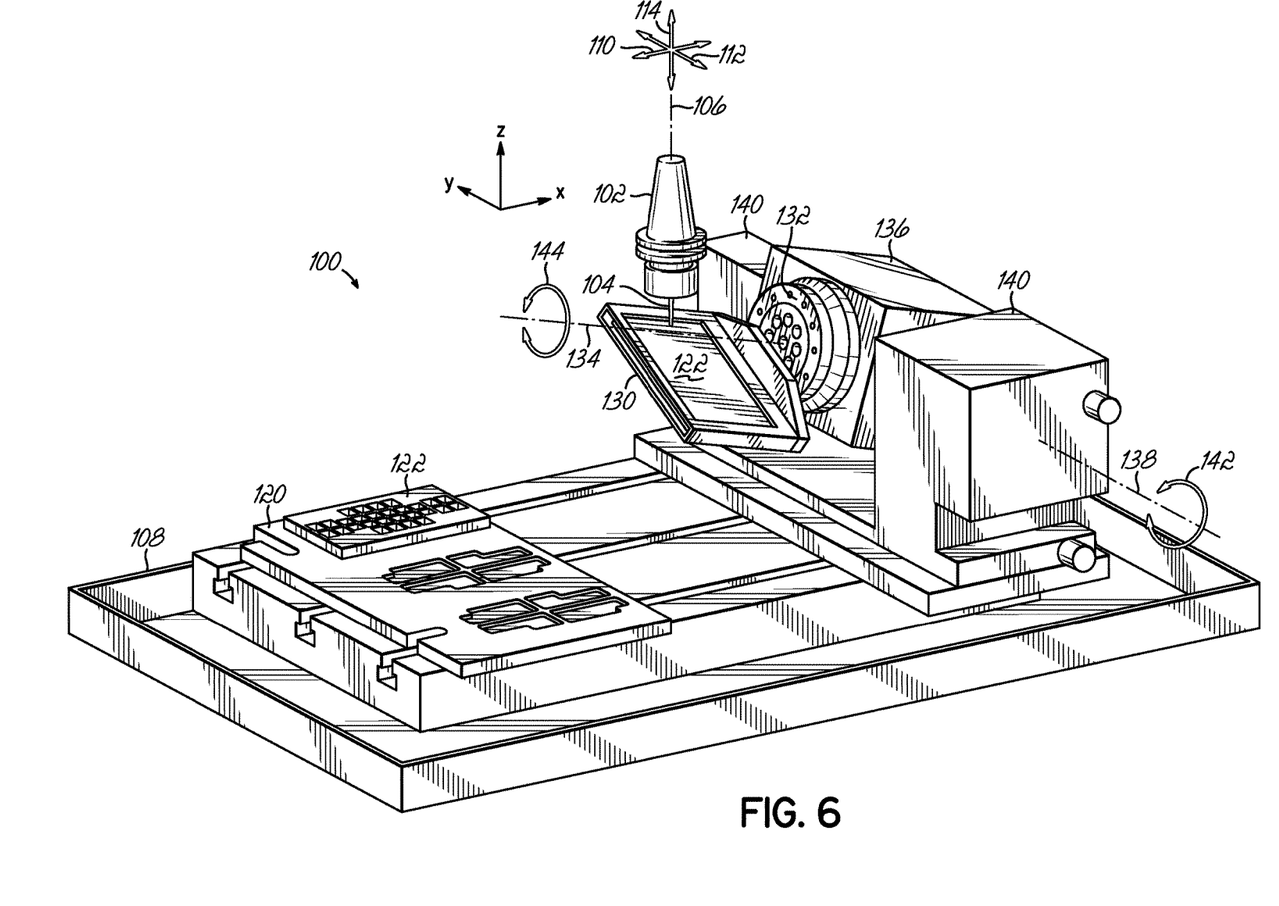
FIG. 6 is a diagrammatic perspective view of an apparatus for milling machining the jig bodies for the jigs of FIGS. 1-5.

FIG. 6 illustrates a numerically controlled milling device 100 that is provided with a rotary milling head 102 that holds a rotary cutting tool bit 104. The bit 104 rotates about a vertical axis in 106 the embodiment shown, although it can be made to operate at some angle with respect to the vertical axis 106. The head 102 is moveable in X, Y and Z directions. The head 102 and the axis of rotation 106 are moveable in the X, Y directions parallel to the horizontal plane, as shown by the arrows 110 and 112, while the head 102 is also moveable vertically in the Z direction on the axis 106, as shown by the arrow 114.

The device 100 is mounted on a stationary base 108, to which are mounted two alternative work holders that hold the material of which the jigs 10 are to be made, preferably the engineering foam material described above. Such material is created to have an exceptional ability to be machined with precision. One holder 120 is a stationary holder fixed to the base 108, and configured to hold one or more blocks of the foam material 122. When supported on this holder 120, the tool 104 can be maneuvered to form the tooth crown conforming cavities in the jigs and to cut the jigs from the block of material 122. On this holder, the tool 104 can cut upwardly facing and vertical surfaces, but cannot cut undercuts or downwardly facing surfaces unless provided with an undercut tool bit or a head 102 having an axis 106 that can be inclined to the vertical.

A second holder 130 is provided that is supported in such a way that it can hold a block of foam material 122 for machining of jigs at an angle to the horizontal. The holder 130 is supported on a chuck 132 mounted on a shaft (not shown) that is rotatable about an axis 134, The shaft on the axis 134 is rotatably mounted on a block 136 that is further rotatable about a horizontal axis 138 that is perpendicular to the axis 134. The axis 138 is defined by a shaft (not shown) supported on mounting blocks 140 that are fixed to the base 108. A block of foam material 122 that is mounted on the support 130 can be tipped about axis 138 as shown by arrow 142 and about axis 134 as shown by arrow 144, thereby enabling the cutting of undercuts and the forming of downwardly inclined surfaces on the jigs 10. Each of the jigs to be used for placing a complete set of brackets for each individual patients can be machined from a single block of foam material 122.

Those skilled in the art will appreciate that the application of the present invention herein is varied, that the invention is described in certain embodiments, and that additions and modifications can be made without departing from the principles of the invention.

Therefore, the following is claimed:

1. An orthodontic appliance and jig combination comprising:

the orthodontic appliance positioning jig for placing one or more orthodontic appliances on one or more teeth of a group of at least two, but not more than six, adjacent teeth of a patient, the jig comprising:

a rigid jig body having at least two jig-locating, tooth-contact areas each shaped to respectively conform to a corresponding jig-contact area on respective occlusal surfaces of different teeth of the group, the at least two tooth-contact areas having the same geometric relationship to each other on the jig body as the corresponding jig-contact areas have to each other on the teeth of the group when the teeth of the patient are in initial, pretreatment positions, a handle structure attached to a surface of the jig body away from the jig-locating areas and configured to be gripped by a tool for transporting the jig to teeth of the patient; and an appliance receiving structure on the jig body configured for holding at least one orthodontic appliance of a predefined configuration in a fixed position and orientation relative to the jig body to bring a mounting surface of the at least one appliance into contact with a mounting area on a facial or lingual surface of a tooth of the group when the body is registered on the teeth of the group with the at least two jig-locating areas of the body in conforming contact with said areas of the occlusal surfaces of the teeth, the at least two jig-locating, tooth-contact areas being configured to contact and conform to a jig-contact area on the occlusal surface of at least two different teeth of the group, and the appliance receiving structure including at least one receiver on the jig body configured to hold an orthodontic appliance in a fixed position on and relative to the jig body to bring a mounting surface of the appliance, when the body is so registered on the teeth, into contact with a mounting area on a surface of a corresponding tooth of the group that is not contacted by the tooth-contact areas of the jig body; and each receiver having an orthodontic appliance removeably supported thereon having a bonding base configured to be bonded to the crown of the corresponding tooth.

2. The orthodontic appliance and jig combination of claim 1 further comprising:

a coating of uncured dental adhesive on the bonding base of the appliance.

3. The orthodontic appliance and jig combination of claim 1 further comprising:

the jig body is formed of a single piece of machinable material;

the jig-locating areas are machined into said material to conform to the custom shape of the crowns of individual teeth of the orthodontic patient.

4. The orthodontic appliance and jig combination of claim 1 wherein:

the jig body is formed of a single piece of machinable material;

the jig-locating areas are machined into said material to conform to the custom shape of the crowns of individual teeth of the orthodontic patient; and the orthodontic appliance and jig combination further comprises a rigid adhesive forming a breakable bond between jig body and the bracket.

5. The orthodontic appliance and jig combination of claim 1 wherein:

the appliance receiving structure includes a second receiver configured to hold at least one orthodontic bracket and the appliance includes a second orthodontic bracket custom configured for bonding to a tooth of the patient.

6. The orthodontic appliance and jig combination of claim 5 wherein:

the appliance receiving structure includes a third receiver configured to hold at least one orthodontic bracket and the appliance further includes a third orthodontic bracket custom configured for bonding to a tooth of the patient.

7. The orthodontic appliance and jig combination of claim 6 wherein:

the appliance receiving structure includes a fourth receiver configured to hold at least one orthodontic bracket and the appliance further includes a fourth orthodontic bracket custom configured for bonding to a tooth of the patient.

8. A set of orthodontic appliance and jig combinations for placing a plurality of orthodontic appliances that collectively form an orthodontic brace for an individual patient on different teeth of an individual patient, the set comprising a plurality of orthodontic appliance and jig combinations according to claim 1, each orthodontic appliance and jig combination having a jig body machined into the same single piece of machinable material so as to be detachable therefrom;

the jig-locating areas of each jig body being machined into said material to conform to the custom shape of the crowns of individual teeth of the orthodontic patient.

9. The set of orthodontic appliance and jig combinations of claim 8 wherein:

each of the jig-locating areas on each jig body has a coating of releasable dental adhesive thereon.

10. An orthodontic appliance and jig combination comprising:

an orthodontic appliance positioning jig for placing three orthodontic appliances, one on each of three teeth of a group of at least three but no more than six adjacent teeth of a patient, wherein the jig comprises:

a rigid jig body having at least two jig-locating, tooth-contact areas each shaped to respectively conform to a corresponding jig-contact area on respective occlusal surfaces of different teeth of the group, the at least two tooth-contact areas having the same geometric relationship to each other on the jig body as the corresponding jig-contact areas have to each other on the teeth of the group when the teeth of the patient are in initial, pretreatment positions, a handle structure attached to a surface of the jig body away from the jig-locating areas and configured to be gripped by a tool for transporting the jig to teeth of the patient; and an appliance receiving structure on the jig body configured for holding at least one orthodontic appliance of a predefined configuration in a fixed position and orientation relative to the jig body to bring a mounting surface of the at least one appliance into contact with a mounting area on a facial or lingual surface of a tooth of the group when the body is registered on the teeth of the group with the at least two jig-locating areas of the body in conforming contact with said areas of the occlusal surfaces of the teeth, the at least two jig-locating, tooth-contact areas including one area configured to contact and conform to a jig-contact area on the occlusal surface on an endmost one of the teeth of the group, one tooth-contact area configured to contact and conform to a jig-contact area on the occlusal surface on the other endmost one of the teeth of the group, no tooth-contact areas being configured to contact any other than the corresponding endmost tooth of the group, when said teeth are in the initial, pretreatment positions, and the appliance receiving structure including three receivers on the jig body, each configured for holding a different one of three orthodontic appliances in fixed positions and orientations relative to the jig body to bring a mounting surface of each into contact with a mounting area on a facial or lingual surface of each respective one of the three teeth of the group when the body is so registered on the teeth; and three orthodontic appliances, each having a bonding base configured to be bonded to the crown of a different one of the three teeth of the group, each appliance being removably connected by the connecting structure to the body of the jig and positioned relative to the jig-locating areas for locating the bonding base thereof at a respective bonding position on the crown of the respective one of the three teeth of the group.

11. An orthodontic appliance and jig combination comprising:

an orthodontic appliance positioning jig for placing four orthodontic appliances, one on each of four teeth of a group of at least three but no more than six adjacent teeth of a patient, wherein the jig comprises:

a rigid jig body having at least two jig-locating, tooth-contact areas each shaped to respectively conform to a corresponding jig-contact area on respective occlusal surfaces of different teeth of the group, the at least two tooth-contact areas having the same geometric relationship to each other on the jig body as the corresponding jig-contact areas have to each other on the teeth of the group when the teeth of the patient are in initial, pretreatment positions, a handle structure attached to a surface of the jig body away from the jig-locating areas and configured to be gripped by a tool for transporting the jig to teeth of the patient; and an appliance receiving structure on the jig body configured for holding at least one orthodontic appliance of a predefined configuration in a fixed position and orientation relative to the jig body to bring a mounting surface of the at least one appliance into contact with a mounting area on a facial or lingual surface of a tooth of the group when the body is registered on the teeth of the group with the at least two jig-locating areas of the body in conforming contact with said areas of the occlusal surfaces of the teeth, the at least two jig-locating, tooth-contact areas include one area configured to contact and conform to a jig-contact area on the occlusal surface on an endmost one of the teeth of the group, one tooth-contact area configured to contact and conform to a jig-contact area on the occlusal surface on the other endmost one of the teeth of the group, no tooth-contact areas being configured to contact any other than the corresponding endmost tooth of the group, when said teeth are in the initial, pretreatment positions; and the appliance receiving structure includes four receivers on the jig body, each configured for holding a different one of four orthodontic appliances in fixed positions and orientations relative to the jig body to bring a mounting surface of each into contact with a mounting area on a facial or lingual surface of each respective one of the four teeth of the group when the body is so registered on the teeth; and four orthodontic appliances, each having a bonding base configured to be bonded to the crown of a different one of the four teeth of the group, each appliance being removably connected by the connecting structure to the body of the jig and positioned relative to the jig-locating areas for locating the bonding base thereof at a respective bonding position on the crown of the respective one of the four teeth of the group.

* * * * *